United States Patent
Lucassen et al.

(10) Patent No.: US 6,687,520 B2
(45) Date of Patent: Feb. 3, 2004

(54) ANALYSIS OF A COMPOSITION

(75) Inventors: Gerhardus Wilhelmus Lucassen, Eindhoven (NL); Robert Frans Maria Hendriks, Eindhoven (NL); Marjolein Van Der Voort, Eindhoven (NL); Gerwin Jan Puppels, Rotterdam (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/221,386

(22) PCT Filed: Jan. 16, 2002

(86) PCT No.: PCT/IB02/00111

§ 371 (c)(1),
(2), (4) Date: Sep. 11, 2002

(87) PCT Pub. No.: WO02/057758

PCT Pub. Date: Jul. 25, 2002

(65) Prior Publication Data

US 2003/0109774 A1 Jun. 12, 2003

Related U.S. Application Data

(63) Continuation-in-part of application No. 09/912,127, filed on Jul. 24, 2001, now Pat. No. 6,609,015
(60) Provisional application No. 60/262,582, filed on Jan. 18, 2001.

(51) Int. Cl.[7] ................................................. A61B 5/00
(52) U.S. Cl. ...................... 600/322; 356/301; 600/476
(58) Field of Search ............................... 600/145, 316, 600/322, 407, 476, 633, 664, 665

(56) References Cited

U.S. PATENT DOCUMENTS

| 5,370,114 A | * 12/1994 | Wong et al. ............... 600/322 |
| 5,814,820 A | 9/1998 | Dong et al. ............. 250/458.1 |
| 6,069,690 A | 5/2000 | Xu et al. ...................... 356/73 |

FOREIGN PATENT DOCUMENTS

EP 0339582 A2 2/1989 .......... G01N/21/64

* cited by examiner

Primary Examiner—Willis R. Wolfe
Assistant Examiner—Johnny H. Hoang
(74) Attorney, Agent, or Firm—Tony Piotrowski

(57) ABSTRACT

An analysis apparatus, in particular a spectroscopic analysis apparatus, comprises an excitation system (exs) for emitting an excitation beam (exb) to excite a target region during an excitation period. A monitoring system (lso) is provided for emitting a monitoring beam (irb) to image the target region during a monitoring period. The monitoring period and the excitation period being substantially overlap, so that monitoring the target region is maintained during excitation. The analysis apparatus is provided with a tracking system (osc, dcu) to control the excitation system to direct the excitation beam onto the target region.

15 Claims, 5 Drawing Sheets

ANALYSIS OF A COMPOSITION

Figure 1:
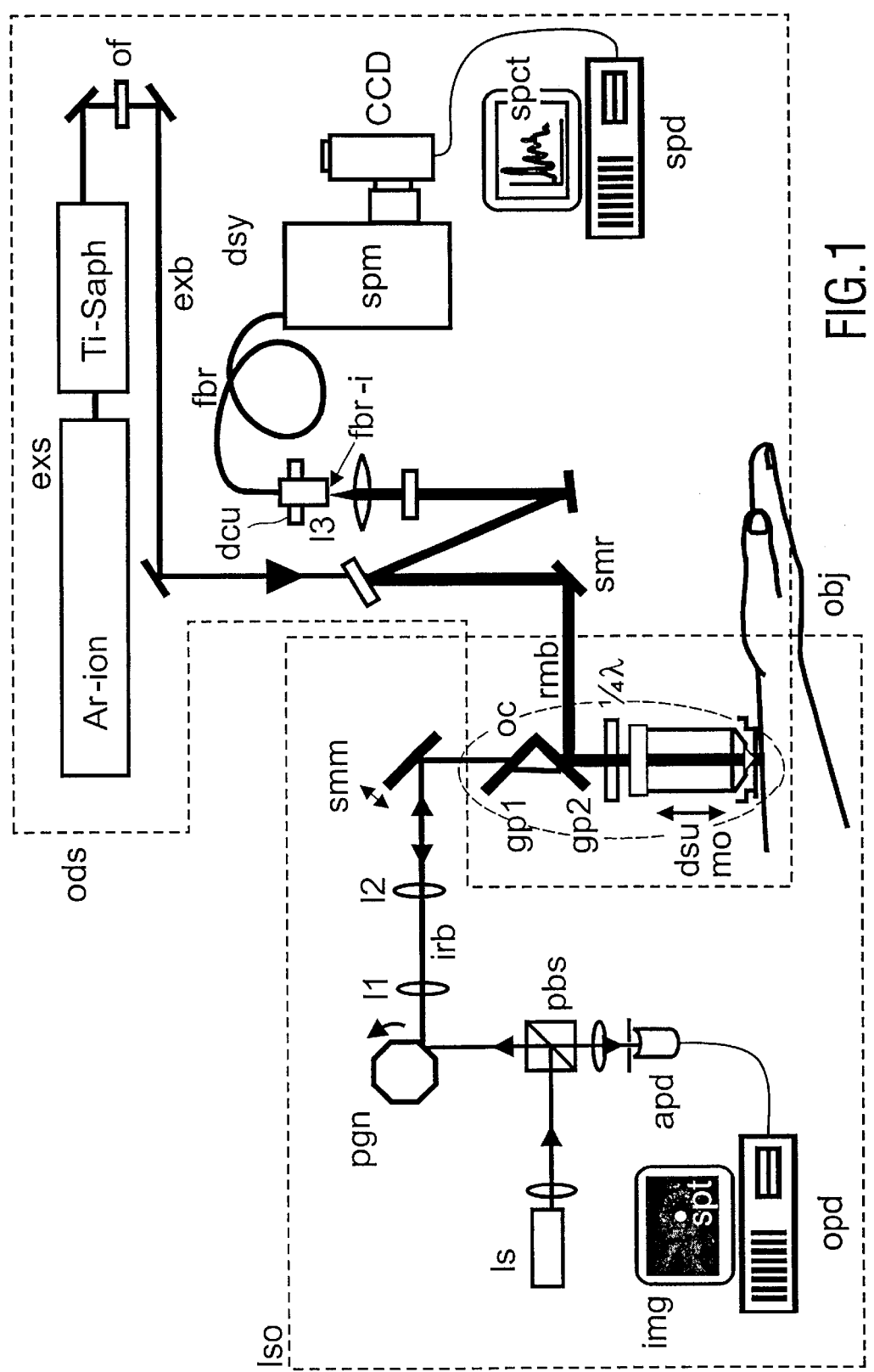

This application is a 371 of PCT/IB02/00111 Jan. 16, 2002; and is a CIP of 09/912,127 Jul. 24, 2001, now U.S. Pat. No. 6,609,015 which claims benefit of 60/262,582 Jan. 18, 2001.

In general, analysis apparatus, such as spectroscopic analysis apparatus are used to investigate the composition of an object to be examined. In particular analysis apparatus employ an analysis, such as a spectroscopic decomposition, based on interaction of the matter of the object with incident electromagnetic radiation, such as visible light, infrared or ultraviolet radiation.

The invention relates to an analysis apparatus, in particular a spectroscopic analysis apparatus, comprising an excitation system (exs) for emitting an excitation beam (exb) to excite a target region during an excitation period a monitoring system (lso) for emitting a monitoring beam (irb) to image the target region during a monitoring period.

Such an analysis apparatus is known from the U.S. Pat. No. 6,069,690.

The known analysis apparatus concerns a dual mode integrated laser imaging and spectral analysis system, which is used to view and analyse defects on a work piece such as a semiconductor wafer. This known analysis apparatus has two operating modes, namely a scanned imaging mode and a stop scan spectral analysis mode. During the scanned imaging mode the monitoring beam in the form of a laser beam is emitted and the target region is imaged. Separately from the imaging, in the stop scan mode, the laser beam is employed for excitation and spectral analysis can be carried out. However, the known analysis apparatus is suitable only for analysis of a stationary object.

An object of the invention is to provide an analysis apparatus that enables accurate analysis of a spatially moving target region.

This object is achieved by an analysis apparatus according to the invention wherein the monitoring period and the excitation period are substantially overlapping and the analysis apparatus is provided with a tracking system (osc, dcu) to control the excitation system to direct the excitation beam onto the target region.

The analysis apparatus of the invention is provided with the tracking system which controls the excitation system notably so as to keep the excitation beam directed to the target region if the target region moves. The tracking system in particular maintains focussing of the excitation beam on the target region. Hence, the excitation of the target region continues while the target region moves and also scattered radiation is being generated by the excitation beam. Thus, the analysis apparatus of the invention can follow a moving detail while continuing the spectroscopic analysis. Hence, the acquisition of spectroscopic data can be integrated in time, even when an appreciable movement of the detail at issue occurs. The signal-to-noise ratio of the spectroscopic data is accordingly increased by the integration. The analysis apparatus of the invention is in particular suitable to perform in vivo Raman spectral analysis of blood in a bloodvessel in the patient's skin. The patient's pulsating blood flow or the patient's muscle movements cause movements of the blood vessels and consequently in the image formed by the monitoring beam the rendition of the bloodvessels move. Especially, appreciable movement can occur of capillary vessels underneath the surface of the patient's skin.

Preferably, the tracking system also controls the monitoring system, notably the tracking system controls focussing of the monitoring beam on the target region. During the overlap of the excitation period and the monitoring period, the excitation of the target region and the monitoring of the target region occur simultaneously and/or alternatingly. Because the target region is imaged together with the excitation, an image is formed displaying both the target region and the excitation area. On the basis of this image the excitation beam can be very accurately aimed at the target region. Consequently, the excitation beam generates scattered radiation almost exclusively in the target region, as at least the target region is included or partly included, in the area that is excited by the excitation beam. The scattered radiation from the target region is detected and the composition of the target region is derived from the scattered radiation. Because the monitoring beam is continuously focused on the spatially moving target region, imaging of the target region and consequently its monitoring is continued even for a moving target, such as a capillary bloodvessel underneath the surface of the skin.

Directing the excitation beam and/or the monitoring beam involves control of the spatial orientation of these beams and also control of the position where these beams are focused. As elaborated with reference to the detailed embodiments, various optical arrangements are suitable to perform such control.

More preferably, both the monitoring beam and the excitation beam are controlled to be directed onto the target region by the tracking system. In this preferred embodiment the monitoring beam is kept directed onto the target region which is then being imaged while the target region moves and meanwhile the target region is being excited by the excitation beam.

In a preferred embodiment of the analysis apparatus of the invention the motion detection system determines the movement of the target region and produces the error signal which represents the motion. The error signal is applied to the tracking system and on the basis of the error signal the tracking system controls the excitation system and/or the monitoring system.

There are various embodiments of the motion detection system. For example, the motion detection system is arranged to receive a series of successive images of the target region. These images preferably also include some of the surroundings of the target region. The images are conveniently supplied by the monitoring system which images the target region by way of the monitoring beam. From the successive images the motion detection system derives the movement of the target. To this end image processing algorithms can be employed which automatically detect the target region from its particular shape and/or its brightness in the successive images being distinct from its surroundings in the images.

In another example the motion detection system receives scattered radiation generated by the excitation beam. In many applications, notably such as Raman spectroscopy of capillary bloodvessels, the intensity or spectral shape of scattered radiation is substantially different from the target region relative to its surroundings. In particular, Raman scattering in pre-selected wavenumber regions from the bloodvessel in the target region is markedly different as compared to Raman scattering from the skin tissue next to the bloodvessel. In this embodiment of the analysis apparatus the motion detection system derives the error signal from the intensity of the (notably Raman) scattered radiation. Especially, the motion detection system is arranged to make successive comparisons of the intensity of the scattered radiation to a reference value to obtain the error signal.

The error signal is then used as a feedback to the tracking system to control the excitation beam and/or the monitoring beam so as to maintain a constant value of the error signal level or keep the signal level of the error signal within predetermined limits, and consequently maintain the intensity of the scattered radiation at a stable level which causes especially the excitation beam to remain being directed onto the target region.

In a further preferred embodiment the analysis apparatus of the invention is provided with a depth setting system to control the focus depth of the monitoring beam and/or the excitation beam. As will be elaborated with respect to the detailed embodiments, various optical arrangements can be employed to control the focus depth of these beams. In a preferred embodiment the depth setting system is arranged to vary the angle of incidence of the monitoring beam on the target region. As a consequence, an object in the focus of the monitoring beam is stationary in the image formed by the monitoring system whereas any images of an object outside of the focus of the monitoring beam is subject to apparent motion owing to parallax. When the target is imaged, its depth is determined on the basis of imaging from various orientations and its apparent motion is observed. Then the excitation beam is focussed at exactly the depth of the target region. Controlling the focus depth of the monitoring and/or the excitation beam is especially advantageous in the application of the analysis apparatus of the invention to Raman spectroscopy of a bloodvessels underneath the skin surface of the patient's skin.

The invention also relates to a method of spectral non-invasive analysis of an object. The method according to the invention is defined in Claim 9. This method is in particular advantageous for spectral non-invasive analysis of blood in vivo.

These and other aspects of the invention will be further elaborated with reference to the embodiments defined in the dependent Claims.

Figure 2:
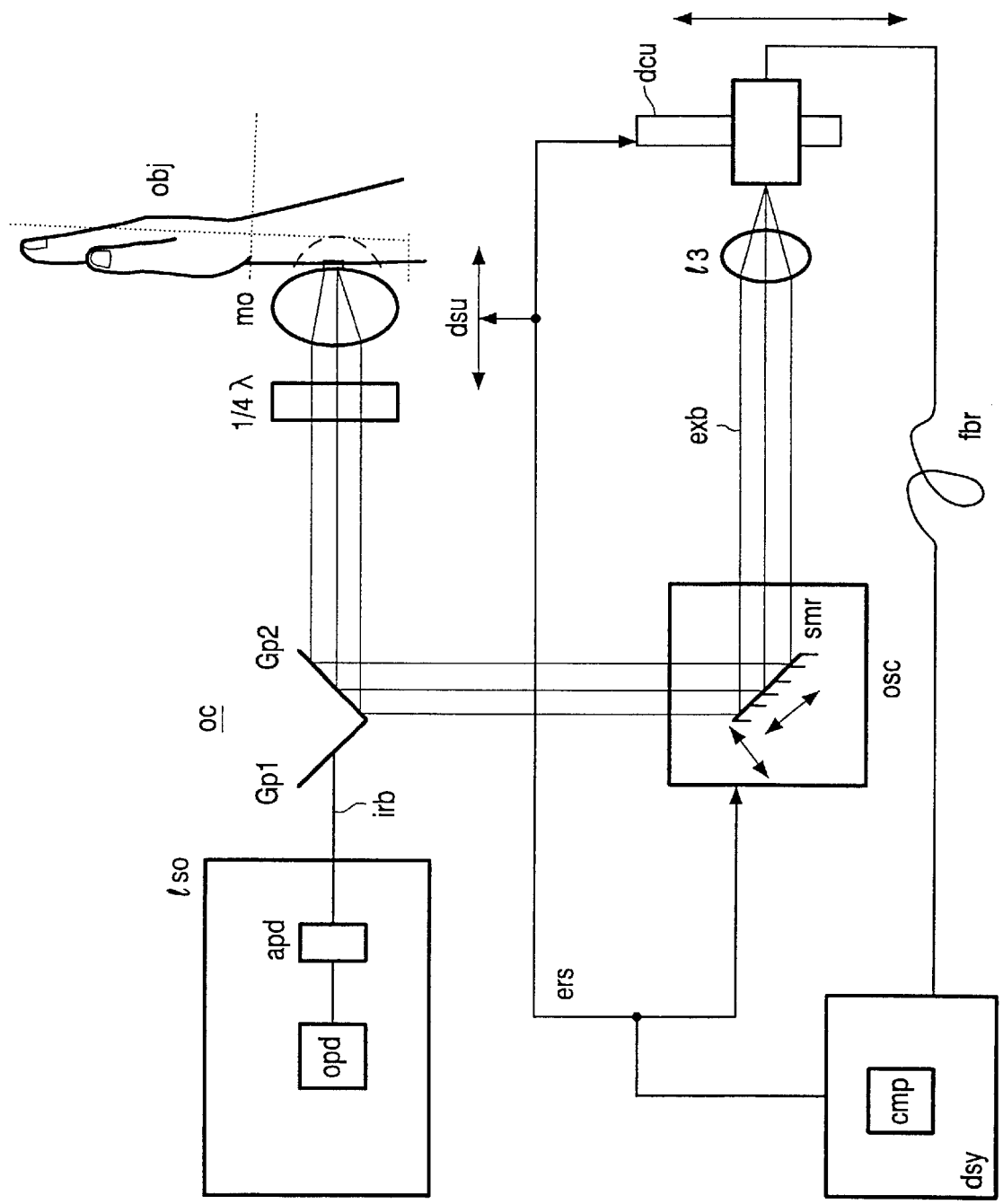
Figure 3:
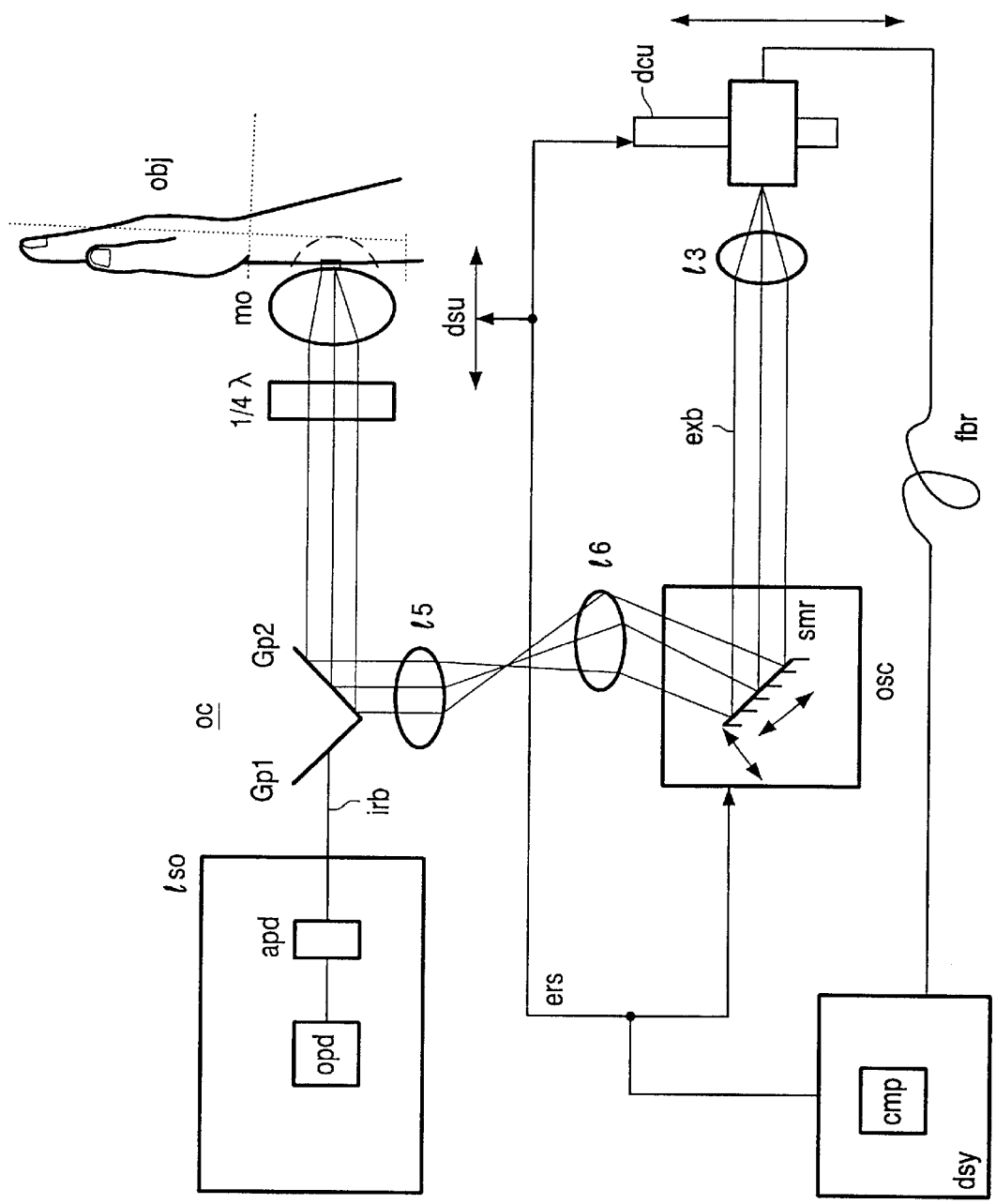
Figure 4:
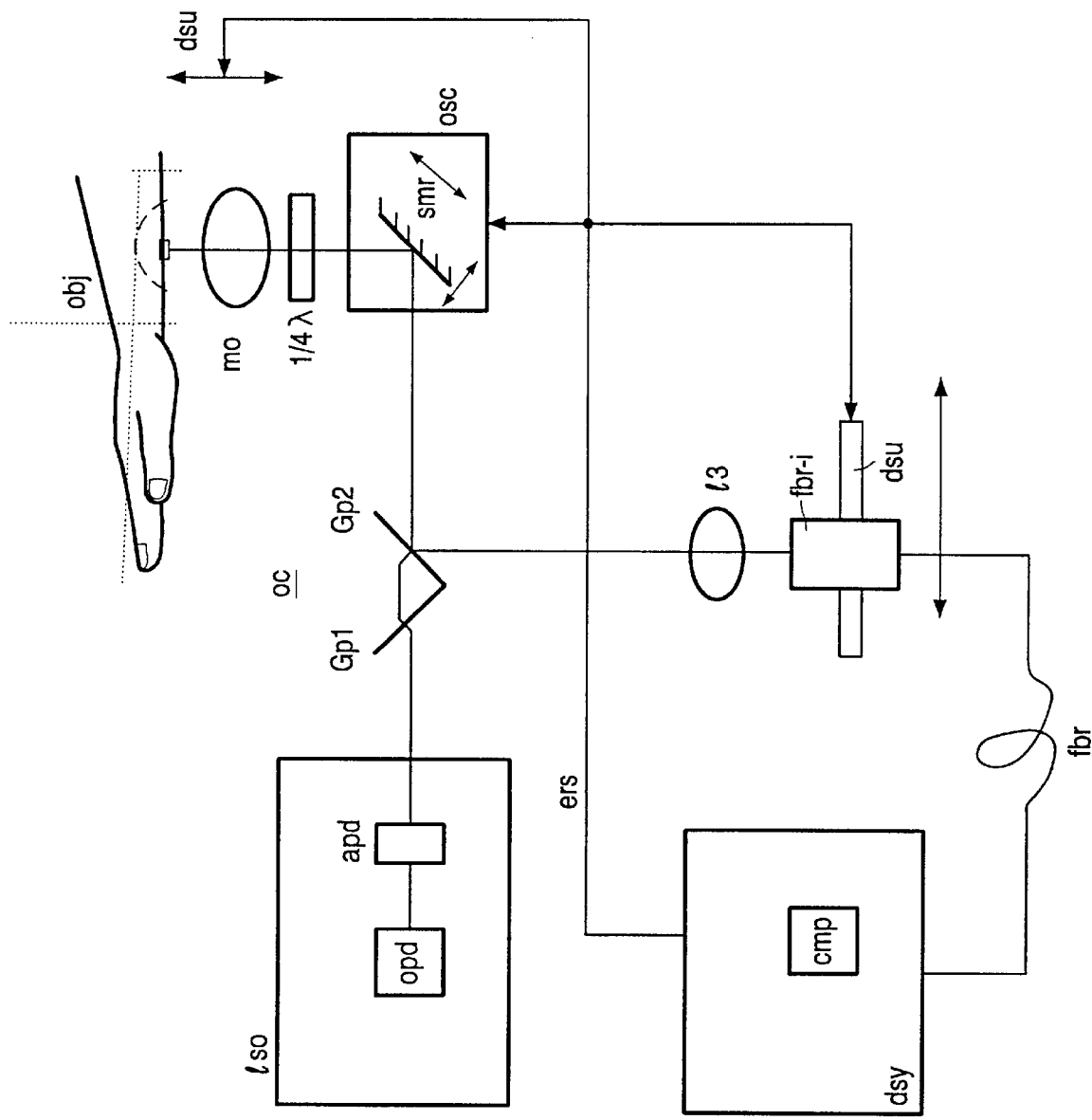
Figure 5:
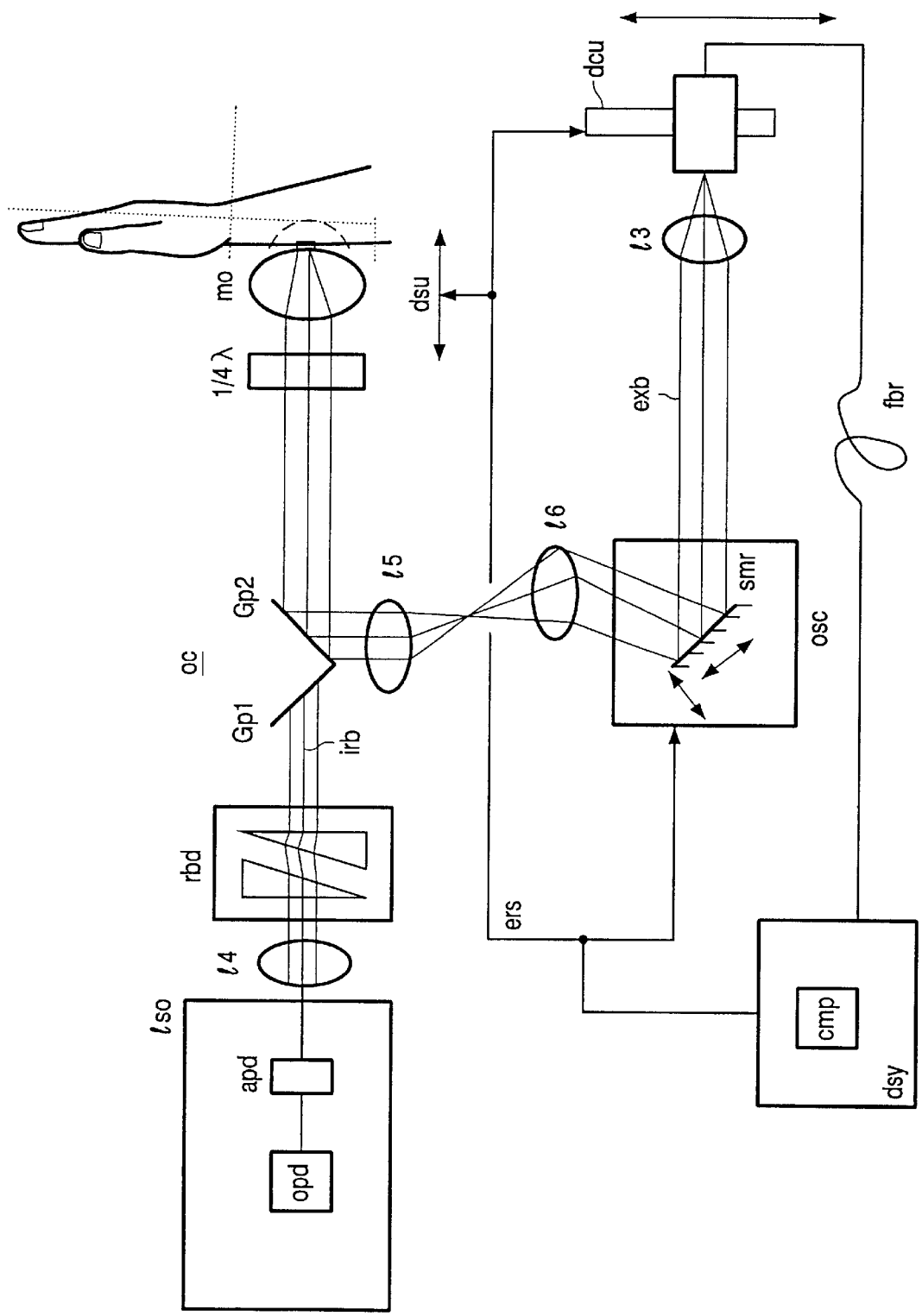

These and other aspects of the invention will be elucidated with reference to the embodiments described hereinafter and with reference to the accompanying drawing wherein FIG. 1 is a schematic representation of an analysis system in accordance with the invention, FIG. 2 is a schematic representation showing details of a preferred embodiment of the tracking system of the analysis system of FIG. 1, FIG. 3 is a schematic representation showing details of another preferred embodiment of the tracking system of the analysis system of FIG. 1, FIG. 4 is a schematic representation showing details of yet another preferred embodiment of the tracking system of the analysis system of FIG. 1, FIG. 5 is a schematic representation showing details of yet another preferred embodiment of the tracking system of the analysis system of FIG. 1, FIG. 1 is a schematic representation of an analysis system in accordance with the invention. The analysis system includes the monitoring system incorporating a light source (ls) with optical imaging system (lso) for forming an optical image of the object (obj) to be examined. The optical imaging system (lso) forms a confocal video microscope. In the present example the object is a piece of skin of the forearm of the patient to be examined. The analysis system also includes for example a multi-photon, non-linear or elastic or inelastic scattering optical detection system (ods) for spectroscopic analysis of light generated in the object (obj) by a multi-photon or non-linear optical process. The example shown in FIG. 1 utilises in particular an inelastic Raman scattering detection system (dsy) in the form of a Raman spectroscopy device. The term optical encompasses not only visible light, but also ultraviolet radiation and infrared, especially near-infrared radiation.

The light source (ls) of the light source the with optical imaging system (lso) is formed by an 834 nm AlGaAs semiconductor laser whose output power on the object to be examined, that is, the skin, amounts to 15 mW. The infrared monitoring beam (irb) of the 834 nm semiconductor laser is focussed in the focal plane in or on the object (obj) by the optical imaging system in the exit focus. The optical imaging system includes a polarising beam splitter (pbs), a rotating reflecting polygon (pgn), lenses (11, 12), a scanning mirror (smm) and a microscope objective (mo). The focussed monitoring beam (irb) is moved across the focal plane by rotating the polygon (pgn) and shifting the scanning mirror. The exit facet of the semiconductor laser (ls) lies in the entrance focus. The semiconductor laser is also capable of illuminating an entrance pinhole in the entrance focus. The optical imaging system conducts the light that is reflected from the focal plane as a return beam, via the polarising beam splitter (pbs), to an avalanche photodiode (apd). Furthermore, the microscope objective (mo) is preceded by a ¼λ-plate so that the polarisation of the return beam is perpendicular to the polarisation of the monitoring beam. The polarising beam splitter (pbs) thus separates the return beam from the monitoring beam. An optical display unit utilises the output signal of the avalanche photodiode to form the image (img) of the focal plane in or on the object to be examined, said image being displayed on a monitor. In practice the optical display unit is a workstation and the image is realised by deriving an electronic video signal from the output signal of the avalanche photodiode by means of the processor of the workstation. This image is used to monitor the spectroscopic examination, notably to excite the target region such that the excitation area falls onto the target region and receiving scattered radiation from the target region.

The Raman spectroscopy device (ods) includes an excitation system (exs) which is in this case constructed as an Ar-ion/Ti-sapphire laser which produces the excitation beam in the form of an 850 nm infrared beam (exb). The Ti-sapphire laser is optically pumped with the Ar-ion laser. Light of the Ar-ion laser is suppressed by means of an optical filter (of). A system of mirrors conducts the excitation beam to the optical coupling unit (oc) and the optical coupling unit conducts the excitation beam along the monitoring beam (irb) after which the microscope objective focuses it in the focal plane at the area of the focus of the monitoring beam.

The optical coupling unit (oc) functions as a beam combination unit. The optical coupling unit conducts the excitation beam along the optical main axis of the microscope objective, that is, along the same optical path as the monitoring beam. The Raman scattered radiation from the target region is reflected to the entrance of a fibre (fbr) by the optical coupling unit (oc). The Raman scattered infrared light is focussed on the fibre entrance in the detection pinhole by the microscope objective (mo) and a lens (13) in front of the fibre entrance (fbr-i). The fibre entrance itself acts as a detection pinhole. The optical imaging system establishes the confocal relationship between the entrance focus, where the semiconductor laser (ls) is present, the exit focus at the area of the detail of the object (obj) to be examined and the detection focus in the fibre entrance (fbr-i). The fibre (fbr) is connected to the input of a spectrometer (spm) with a CCD detector (CCD). The spectrometer with the CCD detector are incorporated in the detector system (dsy) which records the Raman spectrum for wavelengths that are smaller than approximately 1050 nm. The output signal of the spectrometer with the CCD detector represents the Raman spectrum of the Raman scattered infrared light. In practice this Raman spectrum occurs in the wavelength range beyond 730 nm or beyond 860 nm, depending on the excitation wavelength. The signal output of the CCD detector is connected to a spectrum display unit (spd), for example a workstation which displays the recorded Raman spectrum (spct) on a monitor.

The optical coupling unit (oc) includes a partial reflection plate (gp2) and a correction plate (gp1). These partial reflection and correction plates are, for example, glass plates of a thickness of 1.5 mm which are arranged transversely of (preferably perpendicularly to) the plane of the monitoring beam and the excitation beam and also perpendicularly to one another. At the side of the microscope objective the glass plate (gp2) is provided with an optical filter coating in the form of an oxide surface coating (ox) which has a reflectivity of 0.80 for the wavelength ranges 720–740 nm and 860–1050 nm. This glass plate (gp2) acts as the optically selective filter in the form of a beam splitter which separates the Raman scattered light from the monitoring beam. The glass plate (gp2) transmits the infrared light of the monitoring beam practically without attenuation, but the monitoring beam is shifted slightly due to refraction. The correction plate (gp1) shifts the monitoring beam back again, so that the return monitoring beam is accurately focussed onto the avalanche photodiode (apd). The excitation beam that is partly reflected from the object (obj) can also be transmitted to some extent by the optical coupling unit (oc) and the reflected excitation beam can be used to indicate the spot (spt) in the optical image (img) where the excitation beam is incident on the object.

An anti-reflection layer (ar) is provided on both sides of the correction plate. The anti-reflection layers have a reflectivity of less than 0.015 for 834 nm, so that the monitoring beam is hardly reflected.

FIG. 2 is a schematic representation showing details of a preferred embodiment of the tracking system of the analysis system of FIG. 1. This embodiment of the tracking system involves displacing the excitation beam (exb). The excitation beam is for example displaced by displacing the fibre entrance (fbr-i), as indicated by the double arrow. The excitation beam (exb) may also be displaced by way of an optical scanner (osc) which is provided with a scanning mirror (smr). As the excitation beam (exb) is scanned over the object (obj) by the displacement of the fibre entrance (fbr-i), the scanning mirror of the optical scanner or both displacements in combination, the intensity of the scattered radiation from the target and its surroundings in the object varies. The scattered radiation from the object is supplied to the detection system (dsy) by way of the fibre (fbr). The detection system is provided with a comparator unit (cmp) which compares the detected intensity of the scattered radiation to a reference value to produce the error signal that is representing the motion of the target in the object. The error signal (ers) is applied to a fibre displacement control unit (dcu) which controls the displacement of the fibre entrance (fbr-i). Further, the error signal (ers) is applied to the optical scanner (osc) to control the displacement of the scanning mirror (smr). In addition, the error signal may be employed to control the setting of the microscope objective (mo) to set the focus depth of the excitation beam (exb). To this end the microscope objective is provided with the depth setting unit which controls the position of the microscope objective on the basis of the error signal and with respect the object.

FIG. 3 is a schematic representation showing details of another preferred embodiment of the tracking system of the analysis system of FIG. 1. In the embodiment shown in FIG. 3 the tracking system involves a so-called 4f-optical system comprising lenses 15 and 16. In this embodiment the scanning mirror (smr) of the optical scanning system (osc) is scanned over lens 16 and lens 15 produces a parallel beam that is scanned over the object. The scanning mirror (smr) is placed slightly asymmetrically with respect to the optical axis of the excitation beam (exb). In this embodiment there is less need to displace the fibre entrance. Displacing the fibre entrance may even be dispensed with and the optical scanning system itself can move the excitation beam over the object.

In the embodiments shown in FIGS. 3 and 4, the tracking system is formed by the optical scanner (osc) with the displacement control unit (dcu) which functions to direct the excitation beam on the target region while motion occurs. The comparator (cmp) included in the detection system functions as the motion detection system.

FIG. 4 is a schematic representation showing details of yet another preferred embodiment of the tracking system of the analysis system of FIG. 1. The embodiment of FIG. 4 operates quite similarly to the embodiment of FIG. 2, but the optical scanner (osc) is placed adjacent to the microscope objective (mo). In this embodiment, the excitation beam is incident on the same position of the optical coupler (oc) independently of the displacement of the excitation beam relative to the object (obj). Thus, allows further optimisation of the optical coupling unit (oc), notably its filtering function, notably because there is no need to account for variations of the angle and position of incidence of the excitation beam (exb) on the optical coupling unit.

FIG. 5 is a schematic representation showing details of yet another preferred embodiment of the tracking system of the analysis system of FIG. 1. The tracking system shown in FIG. 5 comprises a rotating beam displacer (rbd) which includes a pair of prisms which displace the monitoring beam (irb) laterally with respect to the optical axis of the microscope objective. The pair of prisms can be rotated about an axis perpendicular to the entrance or exit face of the prism-pair. The lateral displacement of the monitoring beam varies as the prism-pair is rotated. Consequently, the monitoring beam (irb) is scanned over the object (obj) and portions of the object that are out-of focus of the monitoring beam experience varying parallax while portions of the object on which the monitoring beam is focussed are imaged stationary in the image (img) of the target region formed by the returning monitoring beam. Hence, the focus depth is easily controlled by adjusting the position of the microscope objective (mo) such that the target region is imaged stationary as the rotating beam displacer scans the monitoring beam. In the embodiment shown in FIG. the tracking system is formed by the optical scanner (osc) with the displacement unit (dsu) to control the excitation beam and the monitoring beam is directed on the target by the rotating beam displacer. In this embodiment, the rotating beam displacer is also used in the motion detection system that further comprises the comparator (cmp).

In the embodiments shown in FIGS. 2 to 5, the optical system (lso) may be arranged as an orthogonal polarised spectral imaging (OPSI) set up instead of a confocal arrangement. Such an OPSI set up does not require the correction plate (gp1), as a CCD sensor is used which can be appropriately positioned

What is claimed is:

1. A spectroscopic analysis apparatus, comprising:
   an excitation system for emitting an excitation beam to excite a target region during an excitation period;
   a monitoring system for emitting a monitoring beam to image the target region during a monitoring period, the monitoring period and the excitation period being substantially overlapping; and
   a tracking system arranged to control the excitation system to direct the excitation beam onto the target region if the target region moves.

2. An analysis apparatus as claimed in claim 1, wherein the tracking system also controls the monitoring system to direct the monitoring beam onto the target region.

3. An analysis apparatus as claimed in claim 1, wherein
   the analysis apparatus is provided with a motion detection system to generate an error signal representing motion of the target region, and
   the motion detection system is coupled to the tracking system to control the excitation system on the basis of the error signal.

4. An analysis apparatus as claimed in claim 2, wherein
   the analysis apparatus is provided with a motion detection system to generate an error signal representing motion of the target region
   the motion detection system is coupled to the tracking system to control the monitoring system.

5. An analysis apparatus as claimed in claim 4, wherein the motion detection system is arranged to
   receive a series of successive image of the target region, and
   derive the error signal from the series of successive images.

6. An analysis apparatus as claimed in claim 4, wherein the motion detection system is arranged to
   receive scattered radiation generated by the excitation beam, and
   derive the error signal from the scattered radiation.

7. An analysis apparatus as claimed in claim 1, further comprising a depth setting system to control the focus depth of the excitation beam and/or the monitoring beam.

8. An analysis apparatus as claimed in claim 7, wherein the depth setting system is arranged to control variation of an angle of incidence of the monitoring beam on the target region.

9. A method for spectral non-invasive analysis of a composition of an object comprising the steps of:
   imaging a target region, during a monitoring period;
   exciting the target region with an excitation beam during an excitation period; and
   if the target region moves, directing the excitation beam onto the target region during an overlap period of the excitation period and the monitoring period.

10. A method as claimed in claim 9, further comprising the step of directing a monitoring beam onto the target region.

11. A method as claimed in claim 9, further comprising the steps of generating an error signal representing motion of the target region; and
    controlling the excitation beam on the basis of the error signal.

12. A method as claimed in claim 10, further comprising the steps of generating an error signal representing motion of the target region; and
    controlling the monitoring beam on the basis of the error signal.

13. A method as claimed in claim 12, further comprising the steps of receiving scattered radiation generated by the excitation beam; and
    deriving the error signal from the scattered radiation.

14. A method as claimed in claim 9, further comprising the step of controlling a focus depth of the excitation beam and/or the monitoring beam.

15. A method as claimed in claim 14, further comprising the step of controlling variation of an angle of incidence of the monitoring beam on the target region.

* * * * *